United States Patent [19]
Kara et al.

[11] Patent Number: 6,143,756
[45] Date of Patent: Nov. 7, 2000

[54] ANTIMALARIAL ACTIVITY OF β-CARBOLINE ALKALOIDS

[75] Inventors: Anna Ursula Kara, Singapore, Singapore; Tatsuo Higa, Nishihara, Japan; Michael Holmes; Kean Hooi Ang, both of Singapore, Singapore

[73] Assignee: National University of Singapore, Singapore

[21] Appl. No.: 09/310,826

[22] Filed: May 13, 1999

Related U.S. Application Data

[60] Provisional application No. 60/085,735, May 15, 1998.

[51] Int. Cl.$^7$ .................................................. A61K 31/44
[52] U.S. Cl. ............................................ 514/281
[58] Field of Search ............................................ 514/281

[56] References Cited

U.S. PATENT DOCUMENTS

| | | | |
|---|---|---|---|
| 4,895,852 | 1/1990 | Higa et al. | 514/281 |
| 4,895,854 | 1/1990 | Higa et al. | 514/281 |
| 5,409,938 | 4/1995 | Boyd et al. | 514/307 |
| 5,639,761 | 6/1997 | Francois et al. | 514/307 |

OTHER PUBLICATIONS

Watanabe et al, J. Nat. Prod., vol. 61, No. 5, pp. 689–692, May 1998.
Edrada et al, J. Nat. Prod., vol. 59, No. 11, pp. 1056–1060, Nov. 1996.
Ann C. Horan, Aerobic Actinomycetes: Sources of Novel Natural Products, Chapter 1., pp. 3–29, in The Discovery of Natural Products with Therapeutic Potential, V.P. Gullo, ed., c. 1994 by Butterworth Heinemann, Boston.
J. C. Hunter–Cerva et al., Aerobic Actinomycetes: Sources of Novel Natural Products, Chapter 2, pp. 31–47, in The Discovery of Natural Products with Therapeutic Potential, V.P. Gullo, ed., c. 1994 by Butterworth Heinemann, Boston.
C. Jaquet et al., Trop. Med. Parasitol., vol. 45, pp. 266–271 (1994).
C. J. Janse et al., Int. J. Parasitol., vol. 24, No. 4, pp. 589–594 (1994).
T. Ichiba et al., Tetrahedron Letters, vol. 29, No. 25, pp. 3083–3086 (1988).
T. Ichiba et al., J. Nat. Prod., vol. 57, No. 1, pp. 168–170 (1994).
T. Higa et al., Chemistry and Toxicology of Diverse Classes of Alkaloids, M. Blum Ed., pp. 337–386 (1996).
J. E. Baldwin et al., Tetrahedron Letters, vol. 33, No. 15, pp. 2059–2062 (1992).
M. H. Heiffer et al., Preclinical Testing, p. 351–373.
S. J. Foote, Acta Tropica, vol. 56, pp. 157–171 (1994).
K. A. El Sayed et al., Journal of Natural Toxins, vol. 5, No. 2, p. 261–287, (1996).
R. A. Edrada et al., J. Nat. Prod., vol. 59, pp. 1056–1060 (1996).
M. M. Dreyfuss et al., Potential of Fungi in the Discovery of Novel, Low–Molecular Weight Pharmaceutcials, pp. 49–79, in the Discovery of Natural Products with Therapeutic Potential, V.P. Gullo, ed., c. 1994 by Butterworth Heinemann, Boston.
F. E. G. Cox, Malaria, Major Animal Models: Rodent,pp. 1503–1543.
A. L. Alger, Rodent Malaria Models, pp. 225–264.
A. D. Kinghorn, The Discovery of Drugs from Higher Plants, pp. 81–108, in The Discovery of Natural Products with Therapeutic Potential, V.P. Gullo, ed., c. 1994 by Butterworth Heinemann, Boston.
G. C. Kirby, Transaction of the Royal Society of Tropical Medicine and Hygiene, vol. 90, pp. 605–609 (1996).
D. L. Klayman, Science, vol. 228, pp. 1049–1055 (1985).
J. Kobayashi et al., Journal of Natural Products, vol. 57, No. 12, pp. 1737–1740 (1994).
K. Kondo et al., J. Org. Chem., vol. 57, pp. 2480–2483 (1992).
G. M. König et al., Planta Med., vol. 60, pp. 532–537 (1994).
E. W. McChesney et al., 4–Aminoquinolines, pp. 5–60.
H. Nakamura et al., Tetrahedron Letters, vol. 28, No. 6, pp. 621–624 (1987).
F. Nosten et al., Drug Safety 12, pp. 264–273 (1995).
P. L. Olliaro et al., Bulletin of the World Health Organization, vol. 73, No. 5, pp. 565–571 (1995).
W. Peters, Parasitology, vol. 90, pp. 705–715 (1985).
J. D. Phillipson, Transactions of the Royal Society of Tropical Medicine and Hygiene, vol. 88, Supp. 1, pp. 17–19 (1994).
J. D. Phillipson et al., Annual Proceedings of the Phytochemical Society of Europe, K. Hostettmann, ed., pp. 49–64 (1987).
Chinese Medical Journal, vol. 92, No. 12, pp. 811–816 (1979).
R. Sakai et al., J. Am. Chem. Soc., vol. 108, pp. 6404–6405 (1986).
T. R. Sweeney, Drugs with Quinine–like Action, pp. 267–324.
H. A. C. Titulaer, J. Pharm. Pharmacol., vol. 42, pp., 810–813 (1990).
D. M. Turner, J. Ethnopharmacology, vol. 51, pp. 39–44 (1996).
N. J. White, J. Antimicrobial Chemotherapy, vol. 30, pp. 571–585 (1992).
N. J. White, Clinical Pharmacokinetics, vol. 10, pp. 187–215 (1985).
A. D. Wright, J. Nat. Prod., vol. 59, pp. 710–716 (1996).

Primary Examiner—James H. Reamer
Attorney, Agent, or Firm—Birch, Stewart, Kolasch & Birch, LLP.

[57] ABSTRACT

Manzamines, administered either intraperitoneally or orally, have been found to prolong survival and inhibit parasitemia in erythrocytic stage malaria. Thus, manzamines can be used for both prophylaxis and treatment. Manzamine A is a preferred compound for use in prophylaxis or treatment.

4 Claims, 8 Drawing Sheets

ANTIMALARIAL ACTIVITY OF β-CARBOLINE ALKALOIDS

This application claims the benefit of U.S. provisional Ser. No. 60/085,735 filed May 15, 1998.

BACKGROUND OF THE INVENTION

1. Field of the Invention

The invention relates to formulations of compounds discovered in marine organisms for pharmaceutical use in treating malaria and to methods of treatment of malaria.

2. The Related Art

The urgency for more new and effective antimalarials escalates as *Plasmodium falciparum* and other human malaria parasite species have developed resistance to most of the commercially available antimalarials[1, 16, 24]. Structurally and functionally novel antimalarial agents are in need as a monotherapeutic agent or for use in combined chemotherapy with other presently available drugs[23]. While most of the antimalarial drugs, for example chloroquine, are products of chemical synthesis, the discovery of artemisinin from the Chinese medical herb *Artemisia annua* L[21, 27] as a potent antimalarial has rekindled interest in screening natural products for new antimalarials[20, 25, 26]. Generally, screening programs focus on terrestrial plant-derived natural products and microbial metabolites due to their abundance and easy accessibility[14, 17, 18, 19, 28]. However, there have been some recent efforts and limited successes in discovery of novel antimalarial compounds from marine organisms[2, 3, 22].

SUMMARY OF THE INVENTION

Manzamines are a unique group of β-carboline alkaloids derived from several sponge species found in Okinawan, Indonesian and the Philippine waters[11, 15]. Manzamine A, the first of the series to be discovered, was initially isolated from sponge Haliclona sp[5] and subsequently from other genera of marine sponges: Pellina[6], Xestospongia[8, 15], Ircinia[9, Pachypellina(7)], and Amphimedon[10]. In addition, several structurally related compounds were characterized from these sponges. The ketonic derivative manzamine F, for example, was isolated from Xestospongia sp[8, 15]. Both manzamine A and manzamine F have previously shown antitumor activity as they were shown to inhibit the growth of P388 mouse leukemia cells in vitro[11]. As part of our screening programs for potential antimalarials derived from marine natural products, these manzamines were evaluated for in vivo antimalarial activity against the asexual erythrocytic stages of rodent malaria parasite *Plasmodium berghei*.

DETAILED DESCRIPTION OF THE INVENTION

Figure 1A:
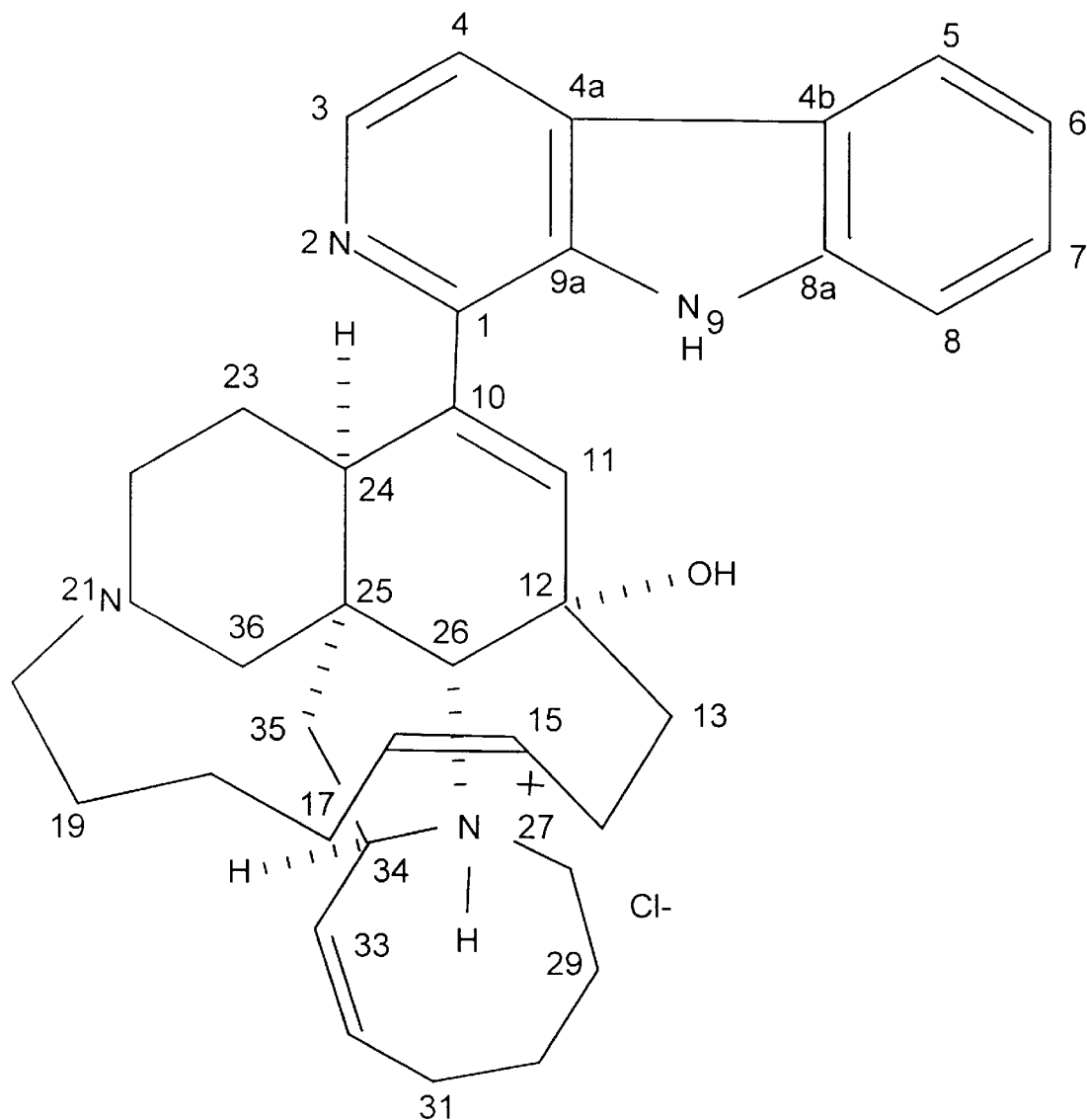
FIGS. 1A and 1B show the structures of manzamine A and manzamine F, respectively.
Figure 1B:
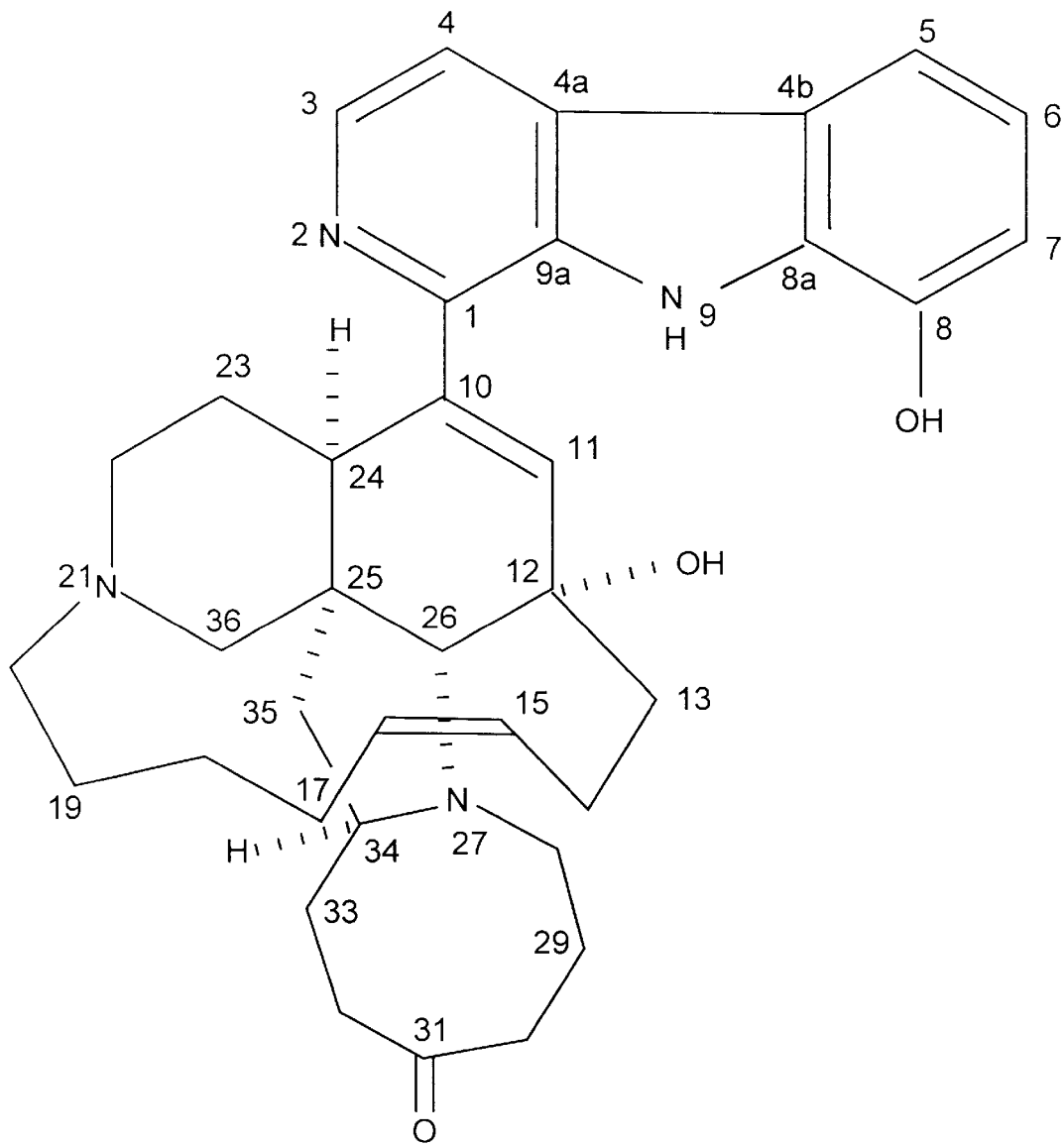

Manzamines are a group of compounds that can be considered ircinal derivatives of carboline, wherein the ircinal moiety is bonded to the 1 carbon of carboline. Exemplary compounds useful in the invention are those wherein the ircinal derivative is ircinal A or ircinal F[11], thus providing manzamine A (the moiety at the 8 carbon of the carboline is H) or manzamine F (the moiety at the 8 carbon of the carboline is keto), respectively. Preferred compounds are those wherein the ircinal moiety includes a double bond between two carbon atoms in an eight atom heterocycle. Typically the group bound to the 8 carbon of the carboline is a hydrogen atom or a hydroxyl; it is preferably a hydrogen atom.

The manzamines of the invention will preferably be isolated from a marine sponge of the genus Haliclona, Pellina, Ircinia, Pachypellina, Xestospongia or Amphimedon. Alternatively, the compounds can be made synthetically, for example as described in references 11, 13 and 31.

The manzamines used in the invention can be obtained as either free bases or as acid salts. The manzamines used can also be administered as pro-drugs. For example, esterification of the C-12 hydroxyl can be accomplished by methods known in the art. Also, reduced forms of manzamines that can be used can be obtained as described in U.S. Pat. No. 4,895,854.

It is within the scope of the invention to combine more than one manzamine compound in a single composition for administration. For example, manzamine A or manzamine F can be combined with any other manzamine compound, for example manzamine D or manzamine B[11]. A preferred combination is one including manzamine A as one of the compounds.

The formulation of alkaloids for pharmaceutical use is considered old in the art. See, e.g. ref. 32, in particular Part 7 thereof. The preferred formulations of the invention are those for intravenous or intramuscular injection, or for oral administration. Pharmaceutical compositions of the invention will typically provide a unit dose of from 10 to 400 μmoles/kg of the manzamine, more typically from 10 to 200 μmoles/kg or 20 to 200 μmoles/kg, still more typically from 50 to 100 μmoles/kg.

The treatment of malaria according to the method of the invention is typically by one-time administration of the anti-malarial composition. However, for some compositions, it might be necessary to administer a plurality of doses over time. An acceptable schedule can be doses providing 10 to 400 μmoles/kg of the manzamine, more typically from 10 to 200 μmoles/kg or 20 to 200 μmoles/kg, still more typically from 50 to 100 μm 20 to 100 μmoles/kg every 24 or 48 hours. Alternatively, similar doses might be administered once per week. The compositions can also be administered for prophylaxis against malarial infection.

The following examples serve to illustrate the invention. The examples are not limiting of the invention, the scope of which is defined only by the claims following.

EXAMPLE 1

Four-week old, male Swiss albino mice were injected intraperitoneally with $10^7$ *P. berghei*-infected mouse erythrocytes. On day 2 after infection, mice were treated with a single i.p. injection of either the test compound or reference drugs (chloroquine or artemisinin) within a concentration range of 50–1,000 µmoles/kg of body weight. All test compounds and reference drugs were injected as a suspension in 5% Tween 60 saline. For oral administration, the test compounds were given as a suspension in corn oil and mice were given two consecutive doses of 100 µmoles/kg of the test compound on days 2 and 3 after infection. Control mice received only 5% Tween 60 saline or corn oil. Survival of the mice was recorded daily. Percentage parasitemia and leucocyte count were determined microscopically from mice tail blood smears that were fixed with methanol and stained with Giemsa.

Blood samples from individual *P. berghei*-infected mice were collected at various time points after a single intraperitoneal treatment of 100 µmoles/kg manzamine A. For transmission electron microscopy, the blood samples were fixed with 3% glutaraldehyde in 0.1M cacodylate buffer (pH 7.4), post-fixed with 1% osmium tetroxide, followed by 1% uranyl acetate, then dehydrated in a graded series of ethanol and embedded in Spurr's resin. Sections were stained with lead citrate and uranyl acetate before viewing under electron microscope.

Manzamine A in serum was detected by liquid chromatography-selected reaction monitoring mass spectrometry (LC-SRM-MS). Blood samples were individually collected from 5 mice treated with manzamine A (100 µmoles/kg i.p.) at specific time points up to 48 hours post-treatment. Serum was isolated by centrifugation and extracted with 95% acetonitrile (MeCN) containing 5 mM ammonium acetate ($NH_4OAc$). The serum extract was filtered and 5 µl samples injected into a Shimadzu LC-10 AD microbore HPLC interfaced with a Perkin Elmer API 300 turbo-ionspray tandem mass spectrometer. Samples were separated on a Prodigy ODS(2) column (30×1 mm, 5 µm) eluted with 50 µl/min of 86% MeNC containing 5 mM $NH_4OAc$. Manzamine A was detected by monitoring the transition of the protonated manzamine A precursor ion from m/z 549.5 $[M+H]^+$ to m/z 531.5 $[M+H-H_2O]^+$. Peak areas for the product ion chromatograms were integrated and concentrations determined from a linear calibration curve of manzamine A in spiked serum. The limit of detection for manzamine A in serum by LC-SRM MS is 2.5 pg.

Results and Discussion

The survival times of mice infected with the erythrocytic stages of *P. berghei* were compared after treatment with a single intraperitoneal injection of either manzamine A, manzamine F, chloroquine or artemisinin (Table 1). All control mice and mice treated with manzamine F died within 4 days post treatment. In contrast, a single intraperitoneal administration of manzamine A (50 or 100 µmoles/kg) prolonged the survival of *P. berghei*-infected mice for more than 10 days with 40% of mice treated with 100 µmoles/kg of manzamine A surviving more than 60 days and recovering with no detectable parasitemia. Similarly, oral administration of an oil suspension of manzamine A significantly prolonged the survival of infected mice (Table 1). The ability of manzamine A and its hydroxyl derivative to extend the lives of infected mice far exceeds that of chloroquine and artemisinin, two of the most important human therapeutic antimalarial drugs. Manzamine A is toxic to mice at 500 µmoles/kg but shows slower acting toxicity than chloroquine, which caused almost instantaneous death of mice treated at 500 µmoles/kg.

A single intraperitoneal injection of manzamine A (50 or 100 µmoles/kg) reduced the parasitemia in mice by more than 90% compared to control mice for the first three days after treatment (Table 2). Such suppressive activity is comparable to that of chloroquine and superior to that of artemisinin at the same dosage. Oral administration (2× 100 µmoles/kg) of manzamine A also produced more than 90% inhibition of parasitemia compared to the control mice for the first three days after the first treatment (Table 2).

Manzamine A appears to have a bioavailability suitable for use in prophylactic applications. Bioavailability of manzamines can be measured, for instance, as described in reference 29.

Figure 2A:
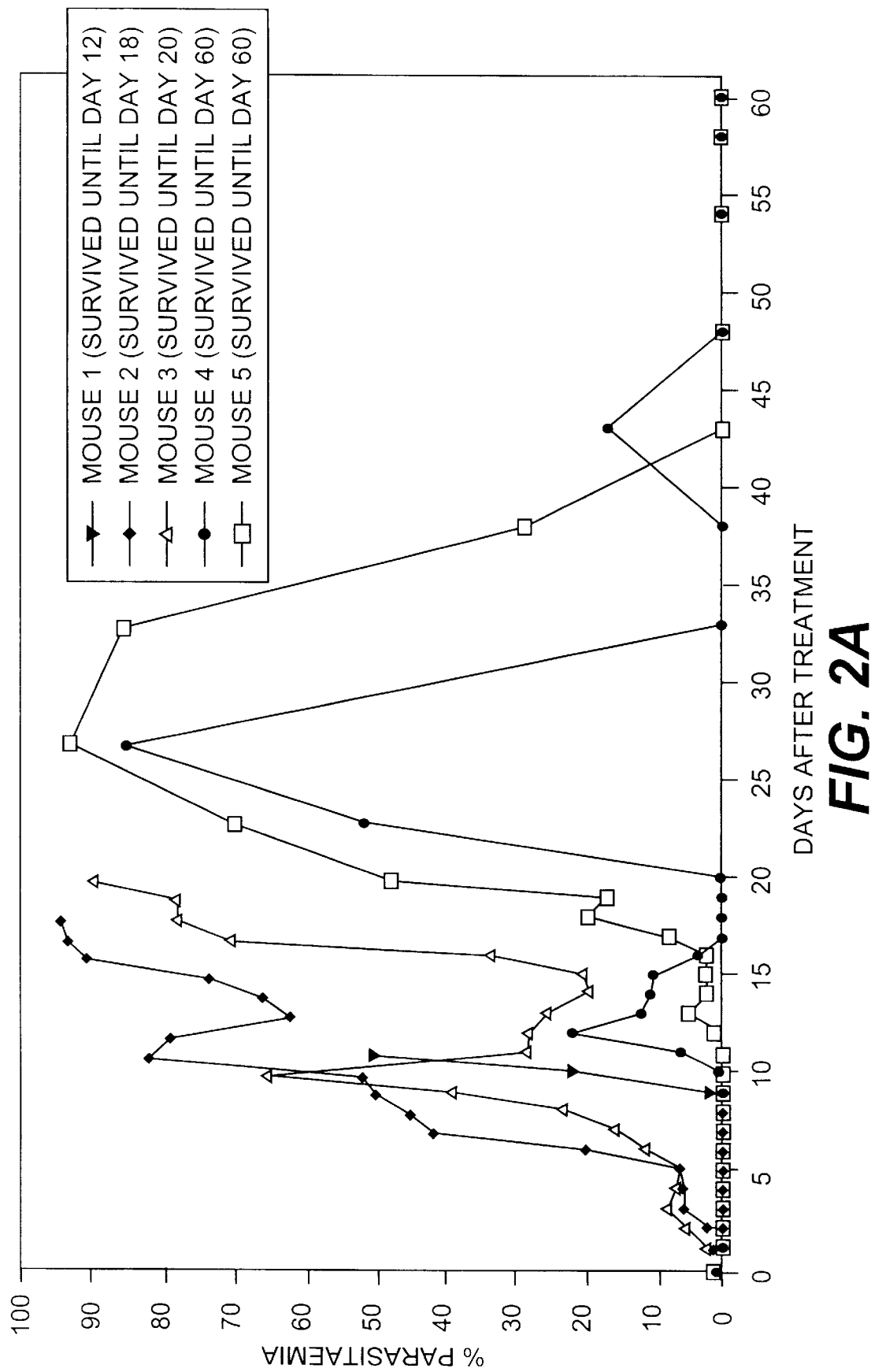
FIG. 2A shows the course of parasitemia in five mice treated with 100 μmoles/kg of manzamine A.
Figure 2B:
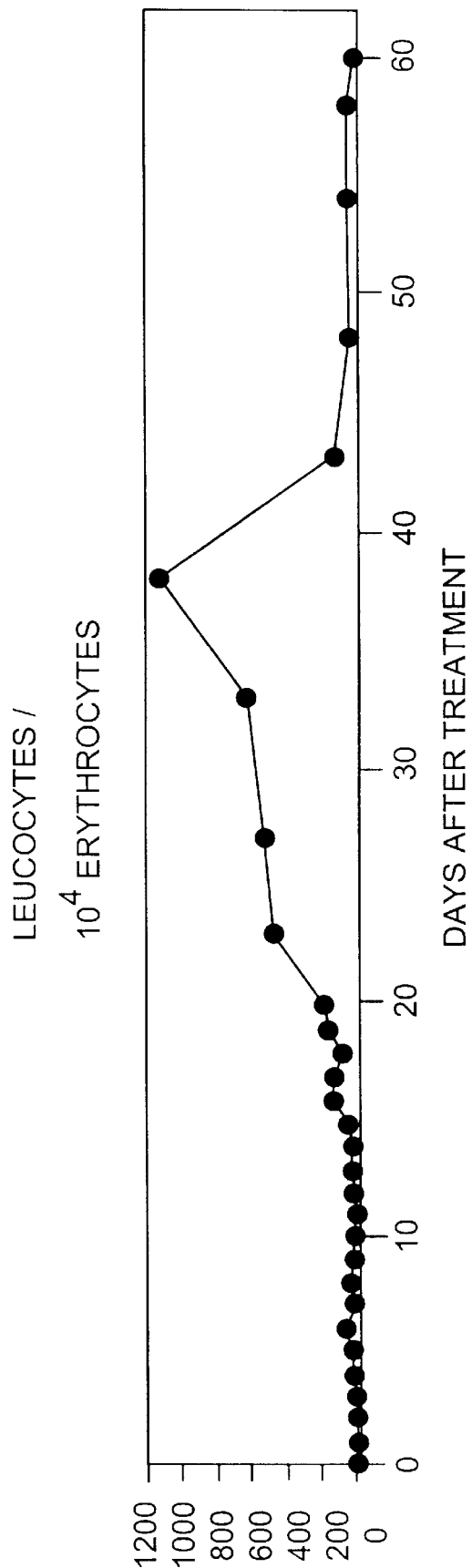
FIGS. 2B–2E show leucocyte counts and percentage parasitemia of two individual mice infected with *P. berghei* and treated with a single intraperitoneal dose of 100 μg/kg of manzamine A. 2B, leucocyte count in mouse 1, which recovered from recurrent parasitemia and survived more than 60 days post treatment; 2C, parasitemia of mouse 1; 2D, leucocyte count of mouse 2; 2E, parasitemia of mouse 2.
Figure 2C:
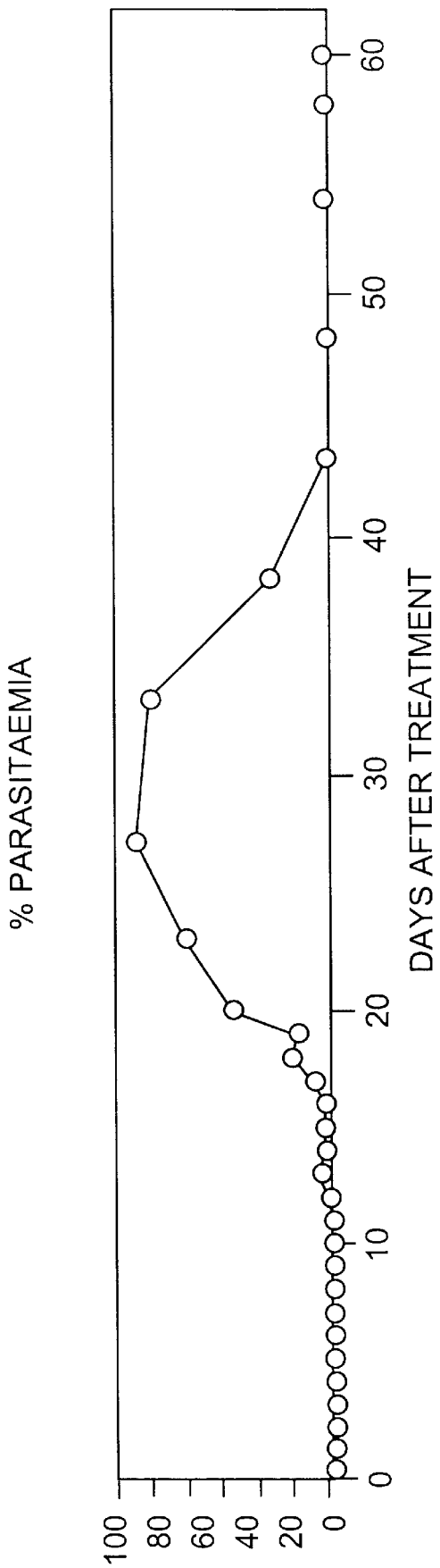
Figure 2D:
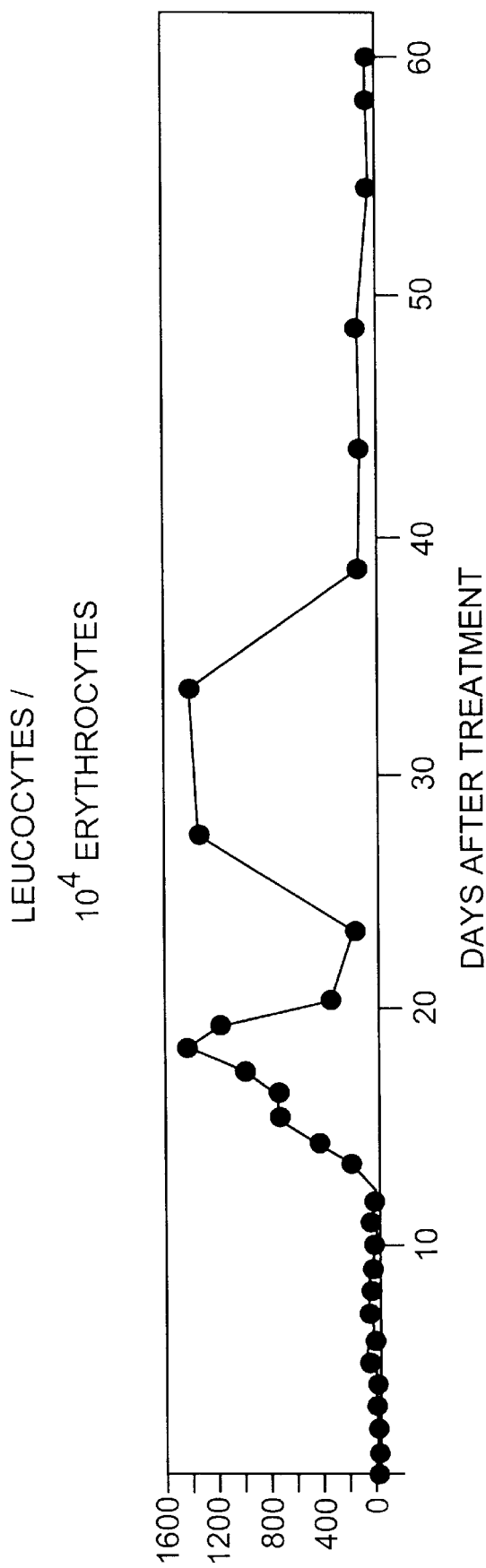
Figure 2E:
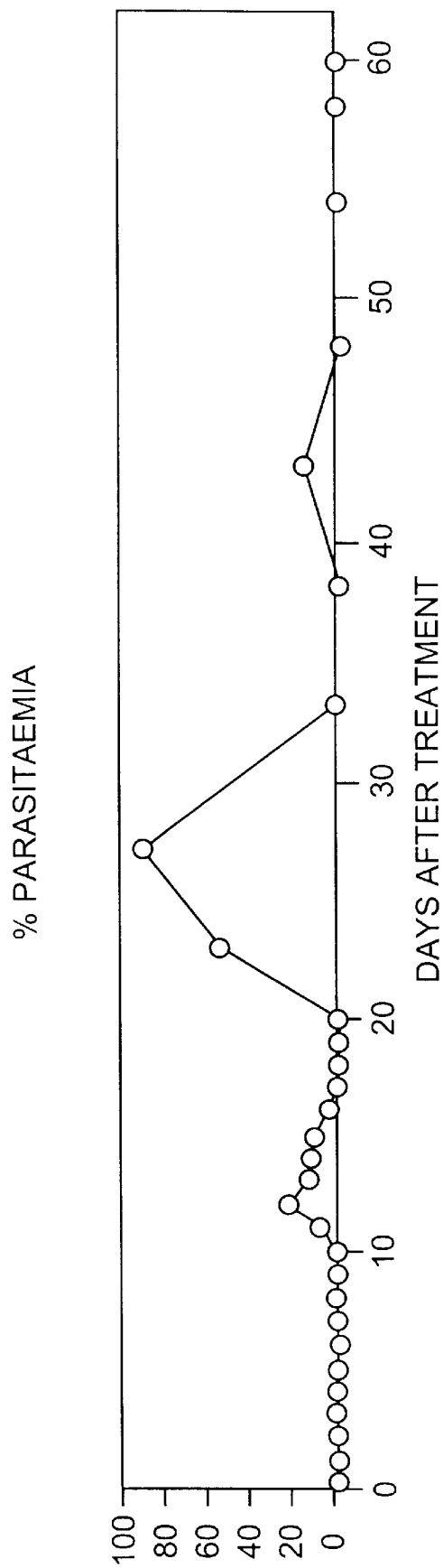

All mice treated with a single dose of manzamine A, chloroquine or artemisinin experienced recurrence of parasites despite the initial suppression of parasitemia development. However, in contrast to chloroquine- and artemisinin-treated mice, most infected mice treated with manzamine A were able to survive for a longer period of time carrying fulminating recurrent parasitemia and two mice were able to clear parasitemia completely. This remarkable fact concurred with a drastic increase in the white blood cell population noted in most manzamine A-treated mice experiencing fulminating parasitemia (FIGS. 2B and 2D). Such an immune response may have been responsible for the eventual recovery of two mice treated intraperitoneally with 100 µmoles/kg of manzamine A (Table 1).

Transmission electron microscopy revealed progressive changes in the morphology of the erythrocytic forms of *P. berghei* parasites after intraperitoneal administration of manzamine A with initial changes seen only 1 hour after injection. One-hour exposure to manzamine A induced the formation of membrane-bound vesicles of varying electron density within the parasites. Four hours after treatment, considerable morphological changes were observed with manzamine A-treated parasites developing increasing electron-dense vesicles. By 12 hours after drug exposure the parasite's cytoplasm showed marked degeneration and was filled with the electron-dense vesicles. Almost all parasites had degenerated by 24 hours after exposure to manzamine A. These morphological changes of *P. berghei* after treatment with manzamine A resemble those reported for chloroquine[16, 30].

Figure 3:
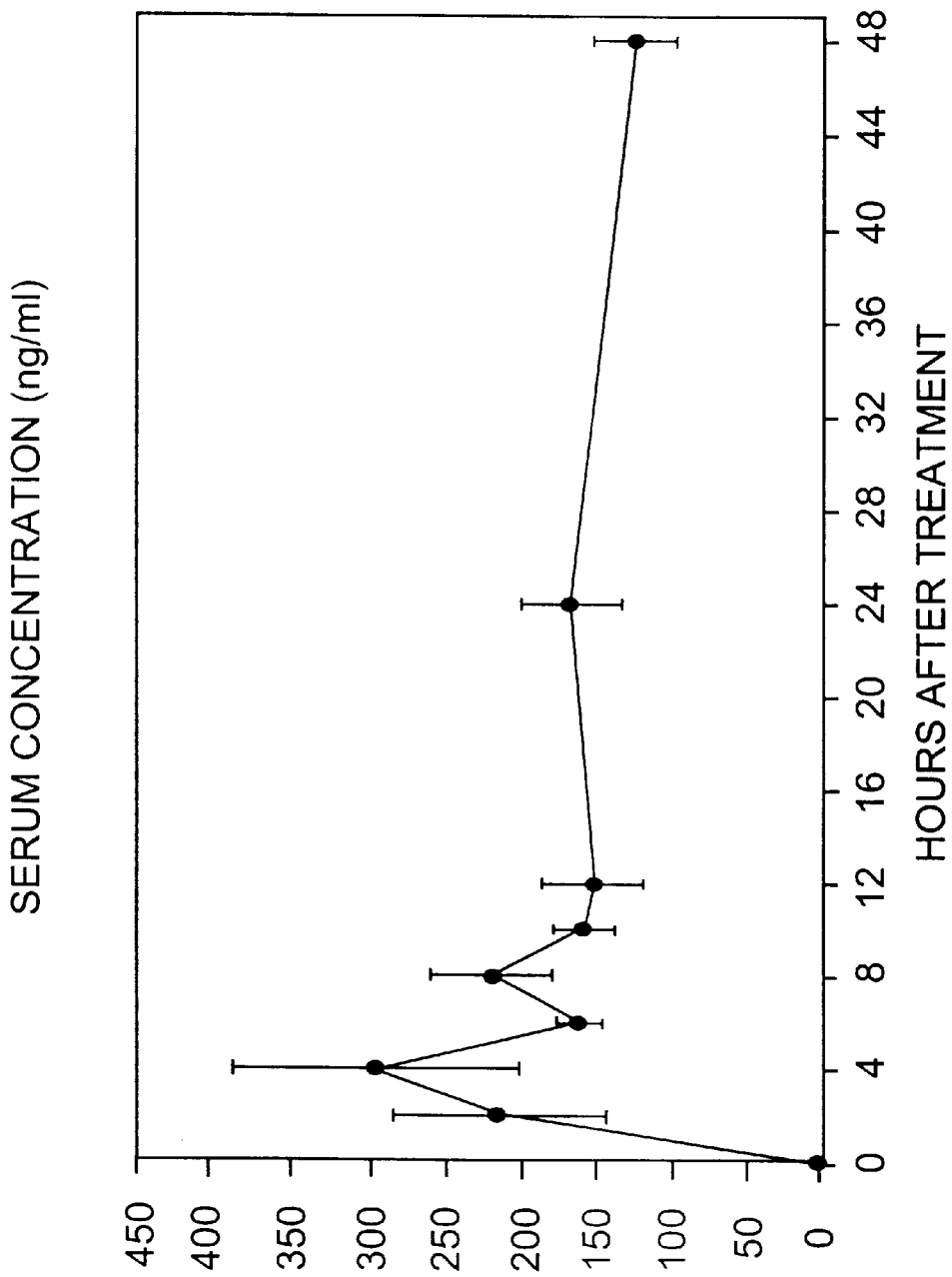
FIG. 3 shows serum concentration (mean ± s.e.) of manzamine A following intraperitoneal administration of 100 μmoles/kg to *P. berghei*-infected mice (n=5).

Pharmacokinetic studies revealed that manzamine A can be detected in *P. berghei*-infected mice showing maximum serum concentrations 4 hours after injection (FIG. 3). Approximately 50% of the maximum serum concentrations were still present in manzamine A-treated mice 48 hours after administration, which may explain the significant inhibition of parasitemia in the infected mice.

EXAMPLE 2

In addition to the in vivo studies in mice, we tested the effectiveness of manzamine A in vitro against the FCR 3 strain of the human malarial parasite *P. faliciparum*, using the standard procedures recommended by the World Health Organization. Manzamine A inhibited the growth of these parasites with an $IC_{50}$<528.8 ng/ml.

TABLE 1

Survival time of *P. berghei*-infected mice treated intraperitoneally (i.p.) or orally with test compounds or reference drugs. Day 0 after treatment corresponds to day 2 after infection. The values are the number of surviving mice/total mice in each treatment group.

| Treatment | | Dose ($\mu$moles/kg) | Mice | 0 | 2 | 4 | 6 | 10 | 15 | 25 | 60 |
|---|---|---|---|---|---|---|---|---|---|---|---|
| Manzamine A | i.p. | 1 × 1000* | 4 | 4/4 | 1/4 | 0/4 | — | — | — | — | — |
| | i.p. | 1 × 500* | 4 | 4/4 | 2/4 | 0/4 | — | — | — | — | — |
| | i.p. | 1 × 100 | 5 | 5/5 | 5/5 | 5/5 | 5/5 | 5/5 | 4/5 | 2/5 | 2/5 |
| | i.p. | 1 × 50 | 5 | 5/5 | 5/5 | 5/5 | 5/5 | 5/5 | 3/5 | 0/5 | — |
| | oral | 2 × 100 | 5 | 5/5 | 5/5 | 5/5 | 5/5 | 4/5 | 0/5 | — | — |
| Manzamine F | i.p. | 1 × 100 | 5 | 5/5 | 5/5 | 0/5 | — | — | — | — | — |
| Artemisinin | i.p. | 1 × 1000 | 5 | 5/5 | 5/5 | 5/5 | 5/5 | 5/5 | 1/5 | 1/5 | 1/5 |
| | i.p. | 1 × 500 | 5 | 5/5 | 5/5 | 5/5 | 5/5 | 1/5 | 0/5 | — | — |
| | i.p. | 1 × 100 | 5 | 5/5 | 5/5 | 4/5 | 0/5 | — | — | — | — |
| | i.p. | 1 × 50 | 5 | 5/5 | 5/5 | 2/5 | 0/5 | — | — | — | — |
| Chloroquine | i.p. | 1 × 1000* | 2 | 0/2 | — | — | — | — | — | — | — |
| | i.p. | 1 × 500* | 2 | 0/2 | — | — | — | — | — | — | — |
| | i.p. | 1 × 100 | 5 | 5/5 | 5/5 | 5/5 | 5/5 | 0/5 | — | — | — |
| | i.p. | 1 × 50 | 5 | 5/5 | 5/5 | 5/5 | 5/5 | 0/5 | — | — | — |
| Control | — | — | 14 | 14/14 | 14/14 | 0/14 | — | — | — | — | — |

*Death of mice due to toxicity upon treatment.

TABLE 2

Percentage parasitemia (mean ± standard deviation) of mice following different treatments for the first three days after treatment. Day 0 after treatment corresponds to day 2 after infection. Control mice died after day 3 post-treatment.

| Treatment | | Dose ($\mu$moles/kg) | Mice | 0 | 1 | 2 | 3 |
|---|---|---|---|---|---|---|---|
| Control | — | — | 14 | 2.1 ± 1.0 | 22.9 ± 8.6 | 57.7 ± 9.9 | 83.5 ± 8.2 |
| Manzamine A | i.p. | 1 × 100 | 5 | 1.4 ± 0.6 | 1.0 ± 1.3* | 1.8 ± 2.8* | 3.1 ± 4.3* |
| | i.p. | 1 × 50 | 5 | 1.8 ± 0.4 | 1.7 ± 1.3* | 2.1 ± 1.7* | 3.4 ± 2.3* |
| | oral | 2 × 100 | 5 | 1.2 ± 0.4 | 2.7 ± 1.5* | 3.2 ± 1.9* | 5.5 ± 6.6* |
| Manzamine F | i.p. | 1 × 100 | 5 | 3.6 ± 0.6 | 22.8 ± 5.1 | 63.1 ± 14.9 | 82.6 ± 7.8 |
| Chloroquine | i.p. | 1 × 100 | 5 | 2.1 ± 0.8 | 1.1 ± 0.4* | 0.2 ± 0.1* | 0.1 ± 0.03* |
| | i.p. | 1 × 50 | 5 | 1.7 ± 0.3 | 1.0 ± 0.6* | 0.3 ± 0.2* | 0.1 ± 0.03* |
| Artemisinin | i.p. | 1 × 100 | 5 | 1.2 ± 0.5 | 2.3 ± 1.8* | 10.4 ± 11.7* | 35.9 ± 20.7* |
| | i.p. | 1 × 50 | 5 | 1.4 ± 0.2 | 4.7 ± 4.8* | 22.2 ± 20.1* | 47.0 ± 23.3* |

*Indicates significant difference from the control ($p < 0.01$).

REFERENCES

1. N. J. White, *J. Antimicrob. Chemother.* 30: 571–585 (1992)
2. K. A. El Sayed et al., *J. Nat. Tox.* 5: 261–285 (1996)
3. A. D. Wright et al., *J. Nat. Prod.* 59: 710–716 (1996)
4. G. M. Konig et al., *Planta Med.* 60: 532 (1996)
5. R. Sakai et al., *J. Am Chem. Soc.* 108: 6404–6405 (1986)
6. H. Nakamura et al., *Tetrahedron Lett.* 28: 621–624 (1987)
7. T. Ichiba et al., *J. Nat. Prod.* 57: 168–170 (1994)
8. T. Ichiba et al., *Tetrahedron Lett.* 29: 3083–3086 (1988)
9. K. Kondo et al., *J. Org. Chem.* 57: 2480–2483 (1992)
10. J. Kobayashi et al., *J. Nat. Prod.* 57: 1737–1740 (1994)
11. T. Higa et al., In M. Blum (ed.), Chemistry and toxicology of diverse classes of alkaloids. Alaken, Colorado, pp. 337–386 (1996)
12. E. Magnier et al., *Tetrahedron* 54: 6201 (1998)
13. J. D. Winker et al., *J. Am. Chem. Soc.* 120: 6425 (1998)
14. M. M. Dreyfuss et al., In V. P. Gullo (ed.), The discovery of natural products with therapeutic potential. Butterworth-Heinemann, Boston pp. 49–80 (1994)
15. R. A. Edrada et al., *J. Nat. Prod.* 59: 1056–1060 (1996)
16. S. J. Foote et al., *Acta Trop.* 56:157–171 (1994)
17. A. C. Horan, In V.P. Gullo (ed.), The discovery of natural products with therapeutic potential. Butterworth-Heinemann, Boston, pp. 3–30 (1994)
J. C. Hunter-Cevera et al. In V.P. Gullo (ed.), The discovery of natural products with therapeutic potential. Butterworth-Heinemann, Boston, pp. 31–47 (1994)
19. A. D. Kinghorn, In V. P. Gullo (ed.), The discovery of natural products with therapeutic potential. Butterworth-Heinemann, Boston, pp. 81–108 (1994)
20. G. C. Kirby, *Trans. R. Soc. Trop. Med. Hyg.* 90: 605–609 (1996)
21. D. L. Klayman, *Science* 228: 1049–1055 (1985)
22. G. M. Konig et al., *Planta Med.* 60: 532–537 (1996)
23. P. L. Olliaro et al., *Bull. W.H.O.* 73: 565–571 (1995)
24. W. Peters, Parasitol. 90:705–715 (1985)
25. J. D. Phillipson, *Trans. R. Soc. Trop. Med. Hyg.*, 88 (Suppl. 1): 17–19 (1994)

26. J. D. Phillipson et al., In K. Hostettmann and P. J. Lea (ed.), Annual Proceedings of the Phytochemical Society of Europe. Clarendon Press, Oxford, pp. 49–64 (1987)
27. Qinghaosu Antimalarial Coordinating Research Group, *Chin. Med. J.* 92: 811–816 (1979)
28. D. M. Turner, 1996. *J. Ethnopharm.* 51: 39–44 (1996)
29. N. J. White, *Clin. Pharmocokinetics* 10: 187–215 (1985)
30. P. B. Mancomber et al., *Nature, Vol.* 214, p. 937 (1967)
31. J. E. Baldwin et al, *Tetrahedron Lett.,* 33:2059–2062 (1992)
32. "Remington: The Science and Practice of Pharmacy", 19th ed., c. 1995 by the Philadelphia College of Pharmacy and Science Articles of the scientific and patent literature cited herein are hereby incorporated in their entirety by reference by such citation.

What is claimed is:

1. A method for treating or preventing malaria comprising administering to a subject a composition comprising Manzamine A.

2. A method of claim 1 wherein said composition is administered in a single dose.

3. The method of claim 1, wherein a dose of Manzamine A of from 10 to 400 $\mu$moles/kg is administered.

4. The method of claim 1, herein a dose of Manzamine A of from 20 to 200 $\mu$moles/kg is administered.

* * * * *